(12) United States Patent
Jackson et al.

(10) Patent No.: US 9,949,760 B2
(45) Date of Patent: *Apr. 24, 2018

(54) POLYAXIAL BONE ANCHOR WITH POLYMER SLEEVE

(71) Applicant: Roger P. Jackson, Prairie Village, KS (US)

(72) Inventors: Roger P. Jackson, Prairie Village, KS (US); James L. Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/426,651

(22) Filed: Feb. 7, 2017

(65) Prior Publication Data

US 2017/0143376 A1  May 25, 2017

Related U.S. Application Data

(63) Continuation of application No. 14/731,064, filed on Jun. 4, 2015, now Pat. No. 9,597,119.

(60) Provisional application No. 62/007,616, filed on Jun. 4, 2014.

(51) Int. Cl.
*A61B 17/70* (2006.01)

(52) U.S. Cl.
CPC ........ *A61B 17/702* (2013.01); *A61B 17/7035* (2013.01)

(58) Field of Classification Search
CPC ............ A61B 17/7037; A61B 17/7032; A61B 17/702; A61B 17/7019; A61B 17/7026; A61B 17/7022; A61B 17/7031; A61B 17/7034; A61B 17/7035
See application file for complete search history.

(56) References Cited

U.S. PATENT DOCUMENTS

| | | |
|---|---|---|
| 8,075,599 B2 | 12/2011 | Johnson et al. |
| 8,444,681 B2 | 5/2013 | Jackson et al. |
| 8,636,778 B2 | 1/2014 | Gephart et al. |
| 2005/0277928 A1 | 12/2005 | Boschert |
| 2007/0233085 A1* | 10/2007 | Biedermann ...... A61B 17/7031 606/86 A |
| 2008/0249576 A1 | 10/2008 | Hawkes et al. |
| 2009/0005817 A1* | 1/2009 | Friedrich ........... A61B 17/7007 606/246 |
| 2010/0087865 A1* | 4/2010 | Biedermann ...... A61B 17/7037 606/264 |
| 2010/0160980 A1 | 6/2010 | Walsh |

(Continued)

OTHER PUBLICATIONS

International Search Report and Written Opinion regarding PCT/US2015/056706, dated Jan. 6, 2016.

(Continued)

*Primary Examiner* — Julianna N Harvey
(74) *Attorney, Agent, or Firm* — Polsinelli PC (57) ABSTRACT

A bone anchor assembly comprising a shank, receiver, pressure insert, sleeve and closure. The sleeve having a body constructed of deformable material and including a transfer of non deformable material molded into the body of the sleeve to transfer force around the body. The receiver having interior guides and the insert having guide followers that cooperate to align the insert in the receiver and prevent rotation of the insert in the receiver.

17 Claims, 12 Drawing Sheets

(56) References Cited

U.S. PATENT DOCUMENTS

| | | |
|---|---|---|
| 2010/0222820 A1 | 9/2010 | Trieu |
| 2011/0178559 A1 | 7/2011 | Barry |
| 2011/0270321 A1 | 11/2011 | Prevost |
| 2012/0109208 A1 | 5/2012 | Justis et al. |
| 2012/0143255 A1 | 6/2012 | Jackson et al. |
| 2013/0110176 A1 | 5/2013 | Rezach et al. |
| 2014/0128927 A1 | 5/2014 | Jackson |
| 2015/0351809 A1 | 6/2015 | Jackson et al. |

OTHER PUBLICATIONS

International Preliminary Report on Patentability regarding PCT/US2015/056703, dated Nov. 17, 2016.

\* cited by examiner

POLYAXIAL BONE ANCHOR WITH POLYMER SLEEVE

CROSS-REFERENCE TO RELATED APPLICATIONS

This application is a continuation of U.S. application Ser. No. 14/731,064, filed Jun. 4, 2015, now U.S. Pat. No. 9,597,119, which claims the benefit of U.S. Provisional Application No. 62/007,616 filed Jun. 4, 2014, each of which is incorporated by reference herein for all purposes.

BACKGROUND OF THE INVENTION

Bone anchors are commonly used in implants to provide an anchored and stable platform for rods, cords and other structure utilized to connect various bones, especially vertebrae. Such implants replace missing bone, support damaged or diseased bone and otherwise support, replace or strengthen the bones, especially the vertebrae of the spine. In certain situations only two vertebrae are joined, whereas in other cases multiple vertebrae are joined.

In general, the art of joining bones using basic system of metal bone screws joined to metal rods is known and established, but does not provide for improvements that give greater flexibility to both the surgeon and the patient.

SUMMARY OF THE INVENTION

A spinal implant system includes bone anchors, which may be bone screws, or structures, such as a hook or the like, that join indirectly to the bone by being joined to a rod that is in turn joined to a bone anchor. The implant system includes at least one bone anchor having a receiver that has a rod or cord receiving channel, a sleeve, and a closure. When the bone anchor is a polyaxial bone screw, such an anchor also includes a threaded shank with an upper capture structure that is received in the receiver and polyaxially rotates therewith during positioning. The anchor preferably also includes a pressure insert located above the shank capture structure for locking the position of the shank when fully assembled. Importantly, the sleeve in this embodiment is made of a non-metallic and flexible or deformable material except for a force transfer structure that is molded or otherwise formed into the sleeve.

An elongate member such as a flexible and tensionable cord is received through a bore in the sleeve. The sleeve is secured in the receiver by advancement of the closure that applies downward force through the transfer structure to the pressure insert which in turn transfers the force to the capture structure of the shank, so as to abut the shank against an interior chamber wall of the receiver either directly or through a retainer to lock the shank in a selected angular position relative to the receiver.

In this manner the transfer structure transfers the force without deforming or otherwise applying damaging force to the flexible sleeve and/or the elongate member.

The receiver includes a series of spaced guides that cooperate with guide receiving structure on the pressure insert to both properly align the insert relative to the receiver when loading the insert into the receiver and to prevent rotation of the insert relative to a central vertical axis of the receiver. The guides allow vertical sliding of the insert relative to the receiver. The receiver and insert can be used with a rod and/or a sleeve, as shown herein.

The drawings constitute a part of this specification and include exemplary embodiments of the present invention and illustrate various objects and features thereof.

DETAILED DESCRIPTION OF THE ILLUSTRATED EMBODIMENT

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
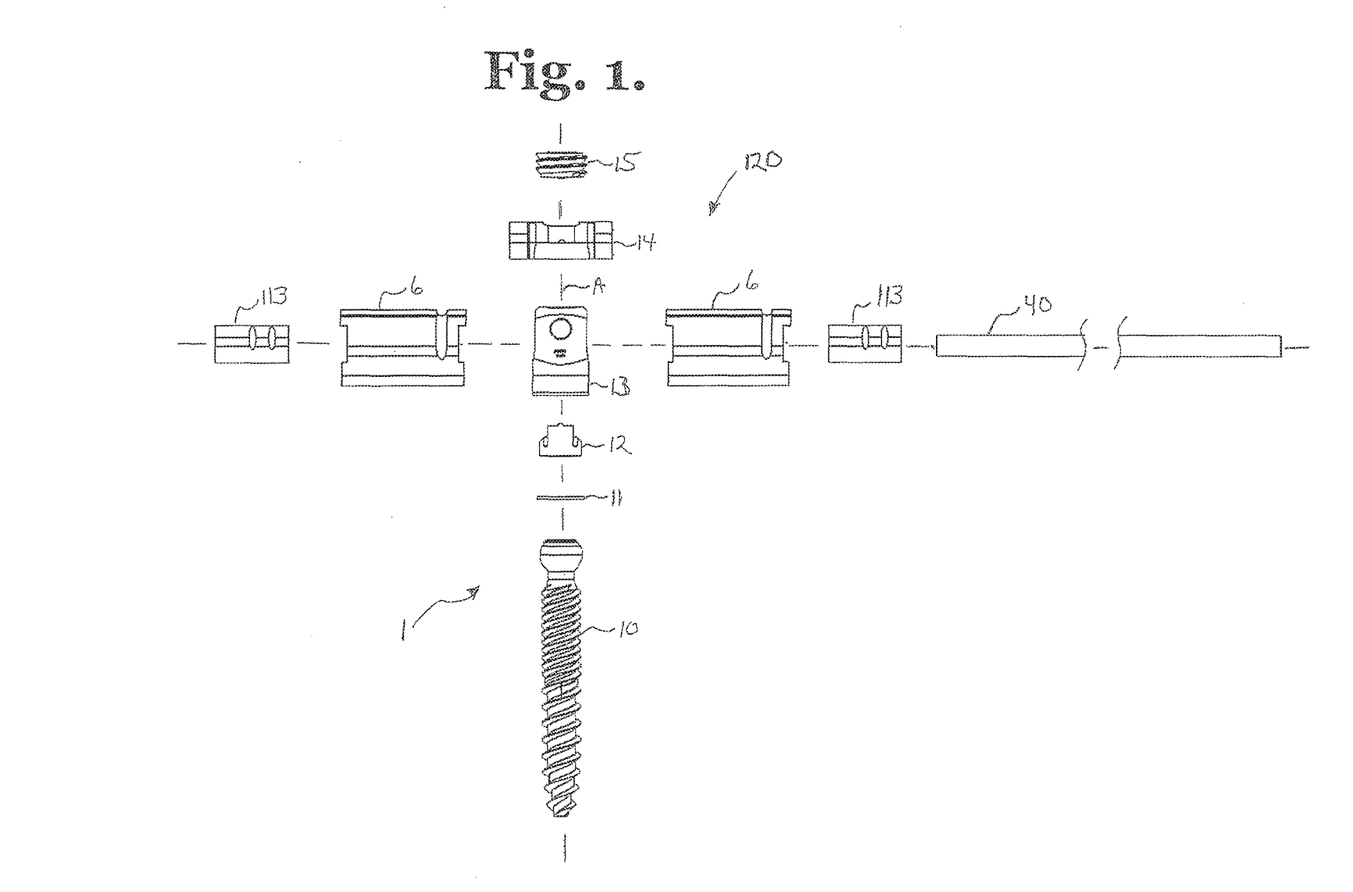
FIG. 1 is an exploded side elevational view of a bone anchor assembly in accordance with the invention, including a shank, a retainer, a pressure insert, a receiver, a sleeve, a closure, a pair of spacers with spacer inserts, and an elongate member.

Illustrated in FIG. 1 is an exploded view of a spinal implant assembly generally indicated by the reference numeral 1. The assembly 1 includes a bone anchor 5 with a spacer 6 and a blocker 7.

The bone anchor 5 is illustrated as a bone screw, however, it is foreseen that the present invention may be utilized with various types of anchors. The bone anchor 5 includes a shank 10, a retainer 11, a pressure insert 12, a receiver 13, a first sleeve 14 and a closure 15.

Figure 6:
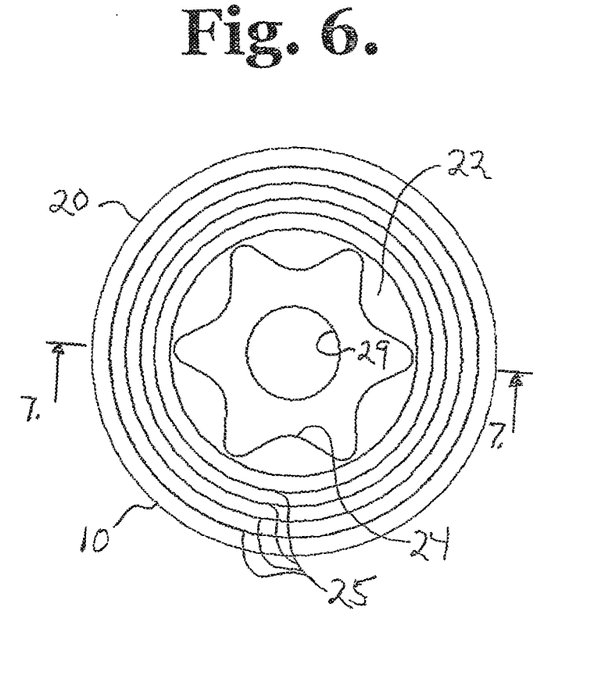
FIG. 6 is a top plan view of the shank.
Figure 7:
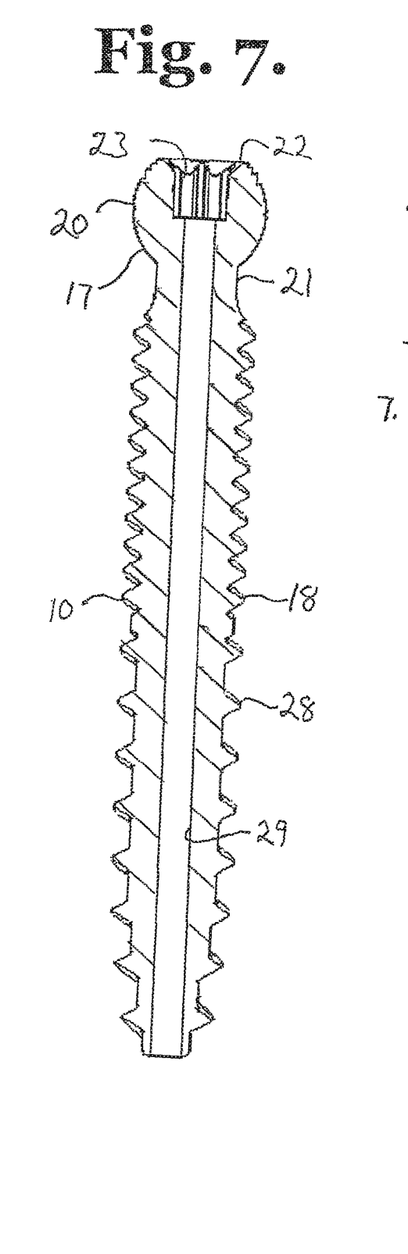
FIG. 7 is a cross sectional view of the shank, taken along line 7-7 of FIG. 6.

The shank 10 has a capture or upper portion 17 and a lower portion 18. The upper portion 17 has a bulbous or partially spherically shaped head 20 and is joined to the lower portion by a neck 21. The head 20 has an upper surface and a central tool engagement structure 23 that has lobes 24 that are adapted to engage a driving tool (not shown) for implanting the shank 10 into a vertebra of a patient. The upper surface 22 also includes a plurality of concentric friction enhancing ribs 25.

The shank lower portion 18 is elongate and has an exterior thread 28 adapted to thread into the vertebra of a patient. The shank 10 has a central bore 29 providing cannulation for insertion over a guide wire during implantation.

The receiver 13 is best seen in FIGS. 8 to 11. The receiver 13 has a lower body 35 with a pair of upstanding and spaced arms 36 and 37 forming a channel 38 therethrough for receiving a rod or a sleeve. The channel 38 has a lower surface 39 that is sized and shaped to be spaced from the bottom half of the elongate member 40, surrounded by the sleeve, or a rod.

Figures 8, 11:
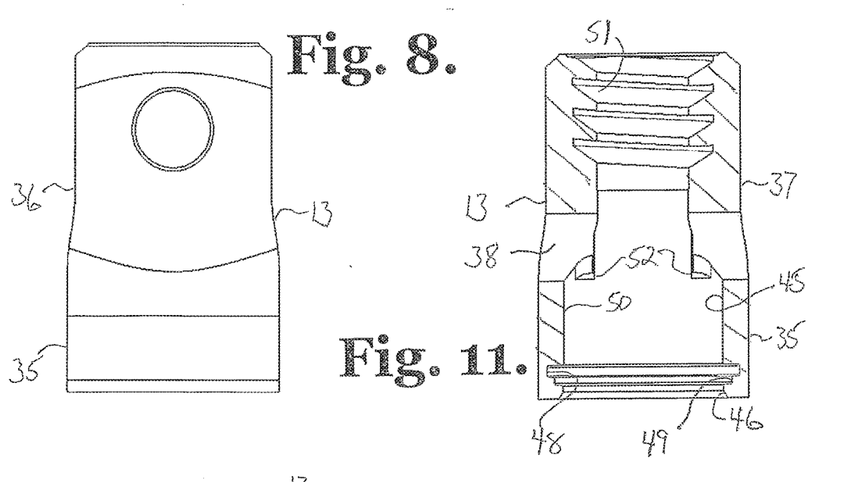
FIG. 8 is a side elevational view of the receiver.
FIG. 11 is a cross sectional view of the receiver, taken along line 11-11 of FIG. 10.
Figure 9:
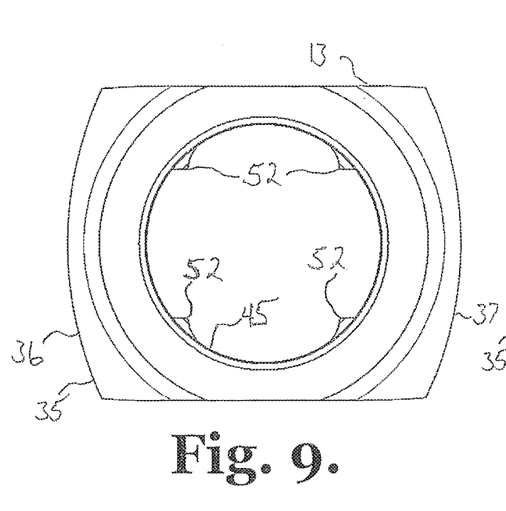
FIG. 9 is a bottom plan view of the receiver.
Figure 10:
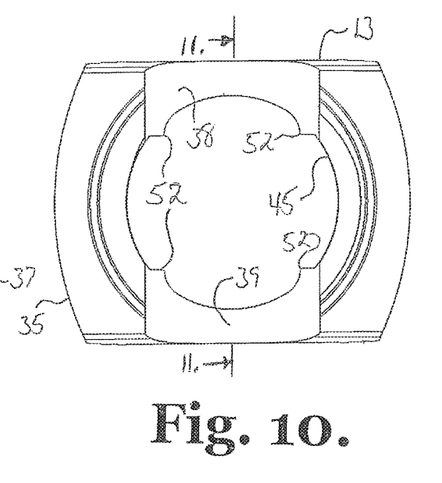
FIG. 10 is a top plan view of the receiver.

The receiver 13 has an interior chamber 45 connecting with the exterior of the receiver 13 through a lower aperture 46, as well as, upwardly joining with the channel 38. Near the lower end of the chamber 45 are located an upper groove 48 and a lower groove 49. The grooves 48 and 49 are concentric, abutting and the upper groove 48 has a somewhat larger diameter than the lower groove 49.

The receiver arms 36 and 37 have inwardly directed and facing sides 50 that include helically wound guide and advancement structure 51 that are shown as reverse angle threads, but may be other types of threads and the like, including V-threads, buttress threads, square threads, rectangular threads and flange forms.

The receiver 13 has a generally vertically aligned central axis A. Mounted in the chamber 45 at spaced locations from each other are four guides 52. The guides 52 are located near the top of the chamber 45 and project generally radially into the chamber 45 relative to the axis A. The guides 52 importantly interact with the insert 12 as discussed below.

Figure 12:
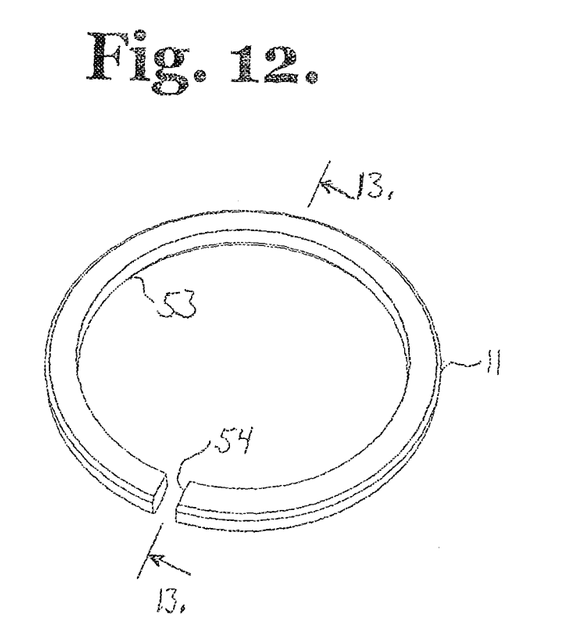
FIG. 12 is a perspective view of the retainer.
Figure 13:
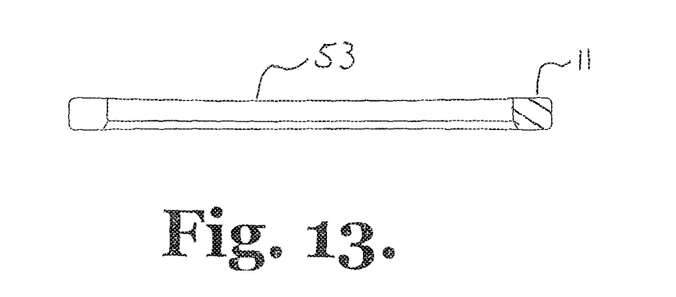
FIG. 13 is a cross sectional view of the retainer taken across line 13-13 of FIG. 12.
Figure 14:
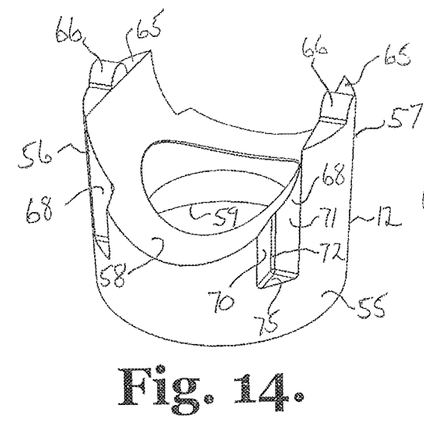
FIG. 14 is a perspective view of the pressure insert.
Figure 15:
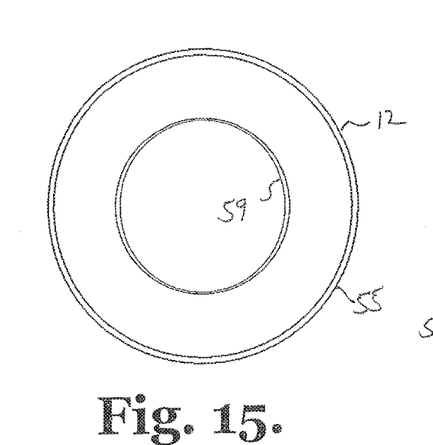
FIG. 15 is a bottom plan view of the pressure insert.
Figure 16:
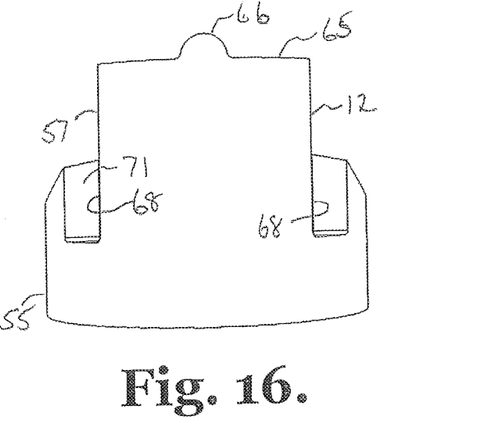
FIG. 16 is a side elevational view of the pressure insert.
Figure 17:
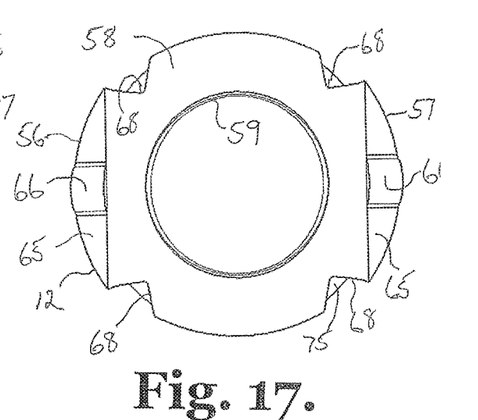
FIG. 17 is a top plan view of the pressure insert.

Shown in FIGS. 12 and 13 is the retainer 11 that includes expandable ring 53 with a gap 54. The retainer 12 is sized to snugly fit into the receiver lower locking groove 49 while being expandable when aligned with the upper expansion groove 48. During assembly, the ring 53 is placed in the chamber 45 and the shank head 20 is pushed therethrough while the ring 53 is aligned with the upper groove 48 after which the shank 10 is lowered until the ring 53 is in the lower groove 49 and thereafter prevented from expanding, thus capturing the shank 10, but allowing the shank 10 to polyaxially rotate during positioning prior to locking.

The insert 12 is best seen in FIGS. 14 to 17. The insert 12 has a lower body 55 with a pair of upstanding spaced arms 56 and 57 forming a U-shaped channel 58 therebetween which aligns with the receiver channel 38. The insert 12 has a bore 59 that aligns with the axis A. At the top of each arm 56 and 57 is a pressure transfer surface 65 each of which has an upward extending and centrally located nub 66. Circumferentially located at equally spaced locations about the body 55 and extending into the arms 56 and 57 are four guide mating structures 68. Each structure includes a pair of vertically aligned walls 70 and 71 that merge at a central vertex 72 to form V-shaped slots that are sized and shaped to receive the guides 52. While V-shaped grooves are illustrated, it is foreseen that the mating structures 68 may have other vertically or axially aligned shapes including slots, indentations, or the like. In this manner, the guides 52 allow the insert 12 to easily slide upward in proper position relative to the receiver while preventing the insert 12 from rotating about the axis A relative to the receiver 13. Located at the bottom of the walls 70 and 71 is a stop 75 that limits the elevation of the insert 12 in the receiver 13 during assembly. The illustrated insert 12 is bottom loaded through the lower receiver aperture 46; however, it is foreseen that the insert 12 may also be top loaded through the chamber 45 in which case the stop 75 would not be utilized.

It is foreseen that the guide mating structure 68 may include corners, shoulders or other features that allow the insert 12 to slide vertically, but that prevent the insert 12 from rotating axially relative to the receiver 13. It is noted that the guide receiving structure 68 and guide 52 cooperation also allows the insert 12 to be easily aligned with and guided into proper position in the receiver 13 during assembly.

Shown in FIGS. 18 to 22 is the first sleeve 14. The sleeve 14 includes a body 80 sized and shaped to fit in the receiver channel 38 between the arms 36 and 37. Extending laterally from the body 80 are a pair of side elements or extensions 81 and 82. As will be noted later, some embodiments have only a single extension. The extensions 81 and 82 mate with the spacers 6. The sleeve 14 has a bore 83 that extends from side to side and is sized and shaped to slidingly receive the elongate member 40. Each extension 81 and 82 includes a vertically aligned abutment or stop surface 85 that is located near the bone anchor 5 in use.

Figure 18:
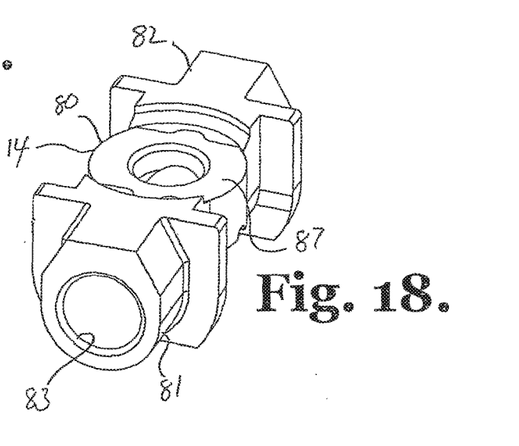
FIG. 18 is a perspective view of the first sleeve of the embodiment of FIG. 1.
Figure 19:
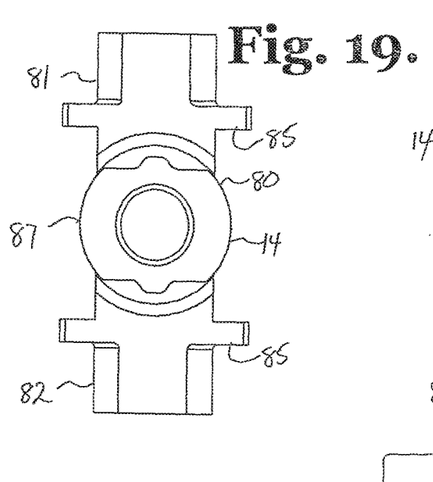
FIG. 19 is a top plan view of the first sleeve.
Figure 20:
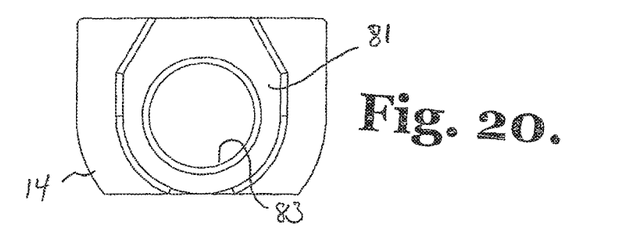
FIG. 20 is a first side elevational view of a first end of the first sleeve with the opposite side being a mirror image thereof.
Figure 21:
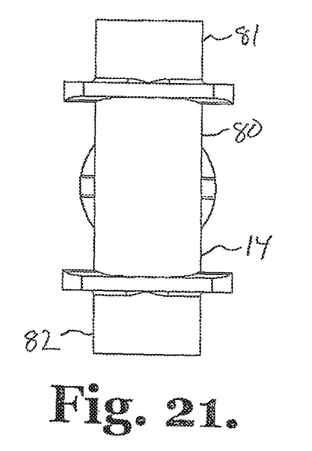
FIG. 21 is a bottom plan view of the first sleeve.
Figure 22:
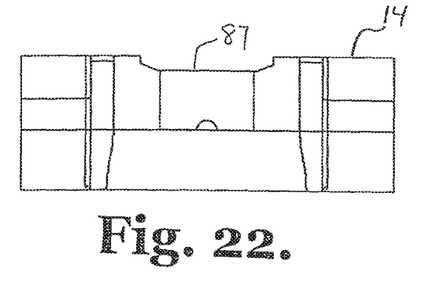
FIG. 22 is a front elevational view of the first sleeve with the rear view being a mirror image thereof.
Figures 23, 24:
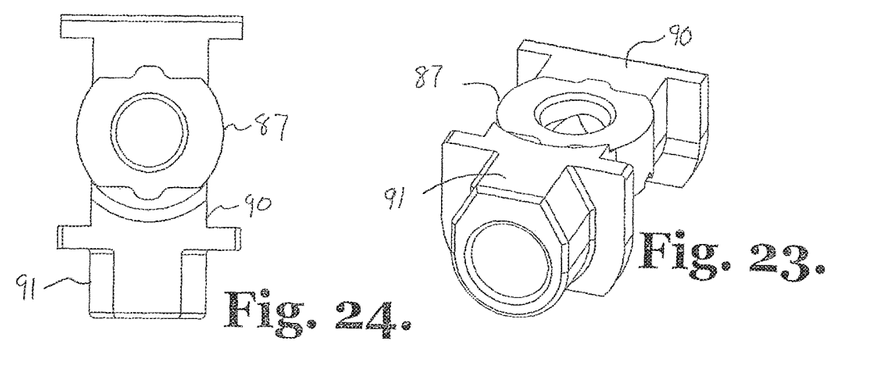
FIG. 23 is a perspective view of the second sleeve used in the embodiment of FIG. 3.
FIG. 24 is a top plan view of the second sleeve.
Figure 25:
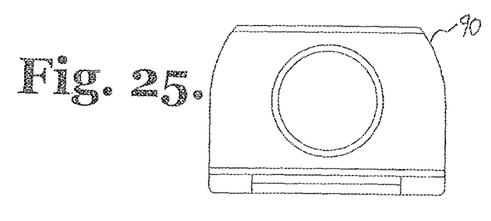
FIG. 25 is a first side elevational view of the second sleeve.
Figure 26:
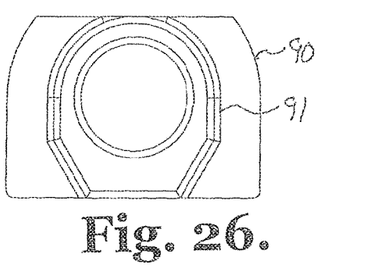
FIG. 26 is a second side elevational view of the second sleeve.
Figure 27:
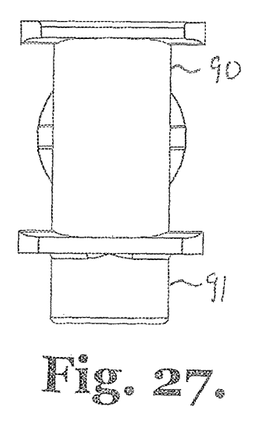
FIG. 27 is a bottom plan view of the second sleeve.
Figure 28:
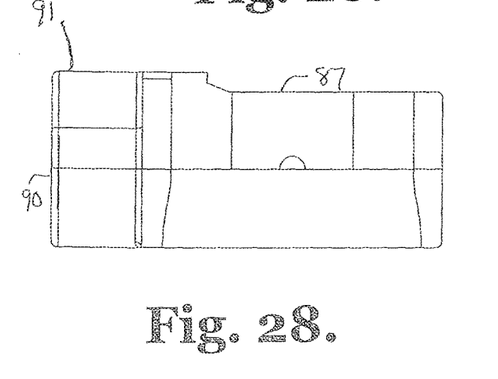
FIG. 28 is a front elevational view of the second sleeve.

Located on the top side and in the middle of the sleeve 14 is a transfer receiving structure 86 that mates with and receives a transfer 87.

The sleeve 14 is constructed of a deformable material that is suited for receiving a pliable, flexible and often elastic elongate member 40 without damaging the member 40 as it slides or moves therein. The sleeve 14 is preferably made of a material such as PEEK (polyether ether ketone), ultra high density polyethylene, various types of polyurethane, especially calcium carbonate filed polyurethane, i.e. PCU, or graphite filed polyurethane, and the like. Such materials while initially being at least somewhat solid, will deform over time in this service due to the pressure exerted thereon by the closure 15. Because of this the materials will creep, or the like, and may cause the strength of the implant 1 to weaken.

The transfer 87 is metallic in nature and is more rigid than the remainder of the sleeve 14, that is, the transfer 87 is designed to be more rigid and less prone to creep than the remainder of the sleeve 14. Preferably, the transfer 87 is made of metal, such as stainless steel, various metal alloys, including such often called cobalt-chrome and cobalt-chrome-molybdenum, titanium, or various titanium alloys and other inplantable metals. The transfer 87 is molded into the sleeve 14 and becomes an integral part of the sleeve 14.

Shown in FIGS. 24 to 28 is a second sleeve 90 that is the same as sleeve 14 except that the sleeve 90 has only one extension 91. The sleeve 90 also includes a molded transfer 87. The purpose of the sleeves 14 and 90 will be discussed below.

The transfer 87 that is seen best in FIGS. 29 to 33 has an upper body 95 with spaced depending legs 96 and 96 forming a saddle shaped structure 98 that is sized and shaped to mate with the top of the sleeves 14 and 90 when molded therein, but also bridge over the elongate member 40 during use. Each of the legs 96 and 97 have lower surfaces 101 that are sized, shaped and positioned to engage and press on the top surfaces of the insert arm top surfaces 65 so as to transfer force exerted by the closure 15, as discussed below, to the pressure insert 12, which force is then transferred to the shank 10 for locking the position of the shank 10 relative to receiver 13. In this manner, the force associated with locking the shank 10 is neither transferred to the elongate member 40 or to the sleeves 14 and 90. Each transfer leg lower surface 101 has an indent 103 that aligns with and snugly receives the nubs 66 on the top of the insert arms 56 and 57 for stability and to resist torsion. Opposed projections 104 extend laterally from each side of the transfer 87 to be imbedded in the sleeves 14 and 90 to resist torquing of the transfer 87 relative to the sleeves 14 and 90 during tightening of the closure 15.

Figures 29, 30, 31, 32, 33:
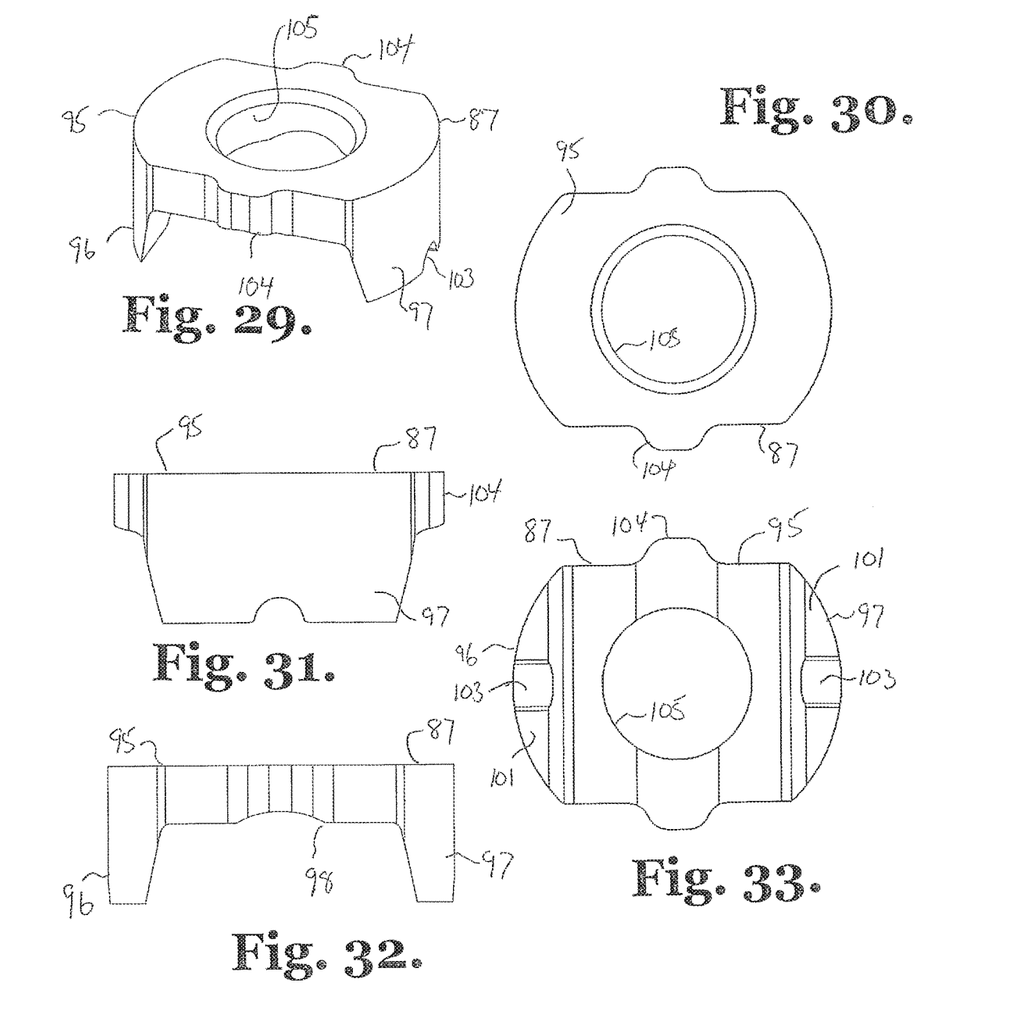
FIG. 29 is a perspective view of a transfer structure utilized with both the first and second sleeves.
FIG. 30 is a top plan view of the transfer.
FIG. 31 is a first side elevational view of the transfer structure with the opposite side view being a mirror image thereof.
FIG. 32 is a front elevational view of the transfer with the rear view being a mirror image thereof.
FIG. 33 is a bottom plan view of the transfer.

The transfer 87 has a vertically and axially aligned passthrough bore 105 to allow passage of various parts of the overall implant assembly 1 in various configurations.

The closure 15 has a cylindrical shaped body 108 with helically wound guide and mating structure 109 that aligns with and rotates into the guide and advancement structures 51 on the receiver arms 36 and 37. A conventional axially aligned drive 110 is utilized to rotate the closure 15. The closure can have a break off head and be configured to penetrate the elongate member such as a cord.

Figure 34:
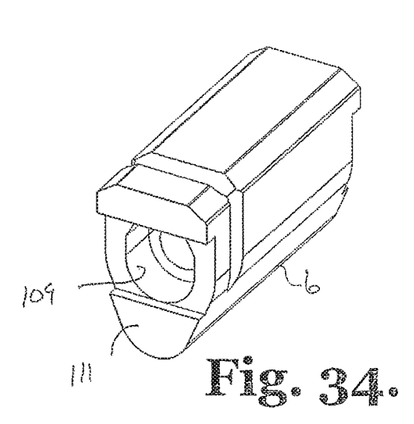
FIG. 34 is a perspective view of the sleeve.
Figure 35:
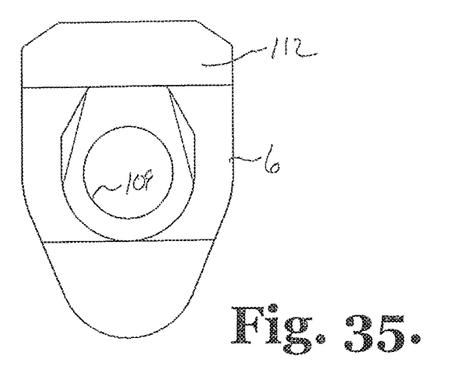
FIG. 35 is a side elevational view of the sleeve.
Figure 36:
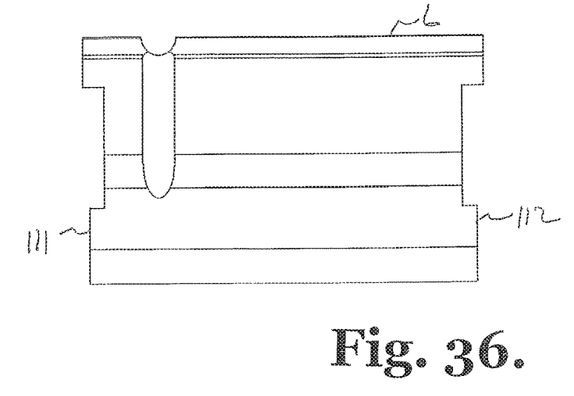
FIG. 36 is a front elevational view of the sleeve.

One of the spacers 6 used in the assembly 1 is illustrated in FIGS. 34 to 36. The spacer 6 includes a body 108 with an elongate passthrough bore 109 sized to slidingly receive the elongate member 40. The spacer 6 includes a relief groove 110 partially around one end and radially positioned with respect to the bore 109 to allow greater flexibility thereat. Opposite ends 111 and 112 of the spacer 6 are sized, shaped and configured to mate with and overlap the sleeve extensions 81 and 82. Each spacer 6 also includes an axial insert 113.

Figure 2:
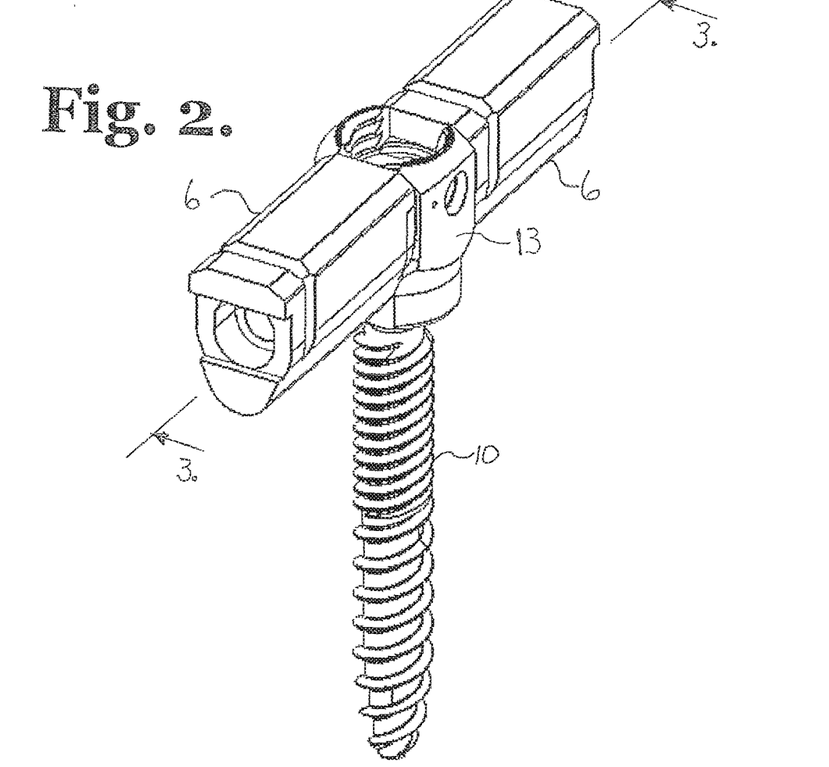
FIG. 2 is a perspective view of the assembly of FIG. 1 fully assembled.
Figure 3:
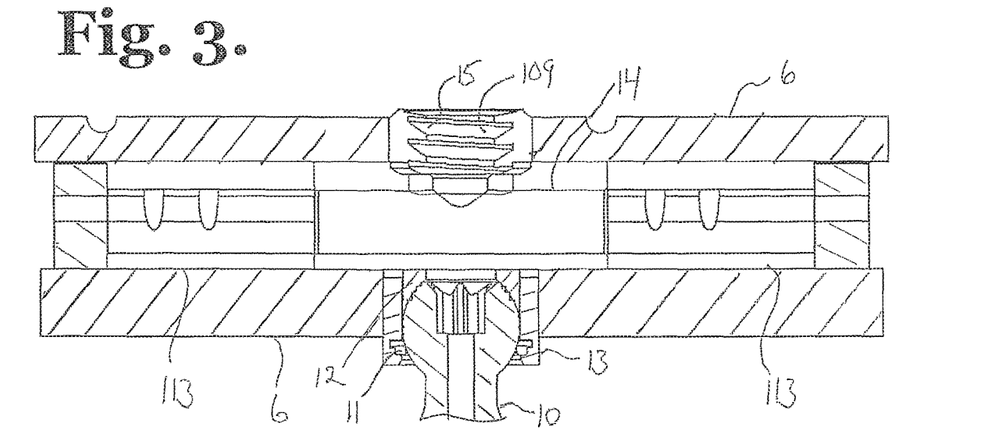
FIG. 3 is a cross sectional view of the assembly of FIG. 2, taken along line 3-3 of FIG. 2.

Shown in FIGS. 1 to 3 is a first configuration 120 of the assembly 1. The configuration 120 is utilized when the bone anchor 5 is positioned between two other bone anchors (not shown). In such a configuration the elongate members will extend between all of the joined bone anchors 5 and spacers 6 will be between each adjacent pair of bone anchors 5. For the configuration 120, the sleeve 14 is utilized.

Figure 4:
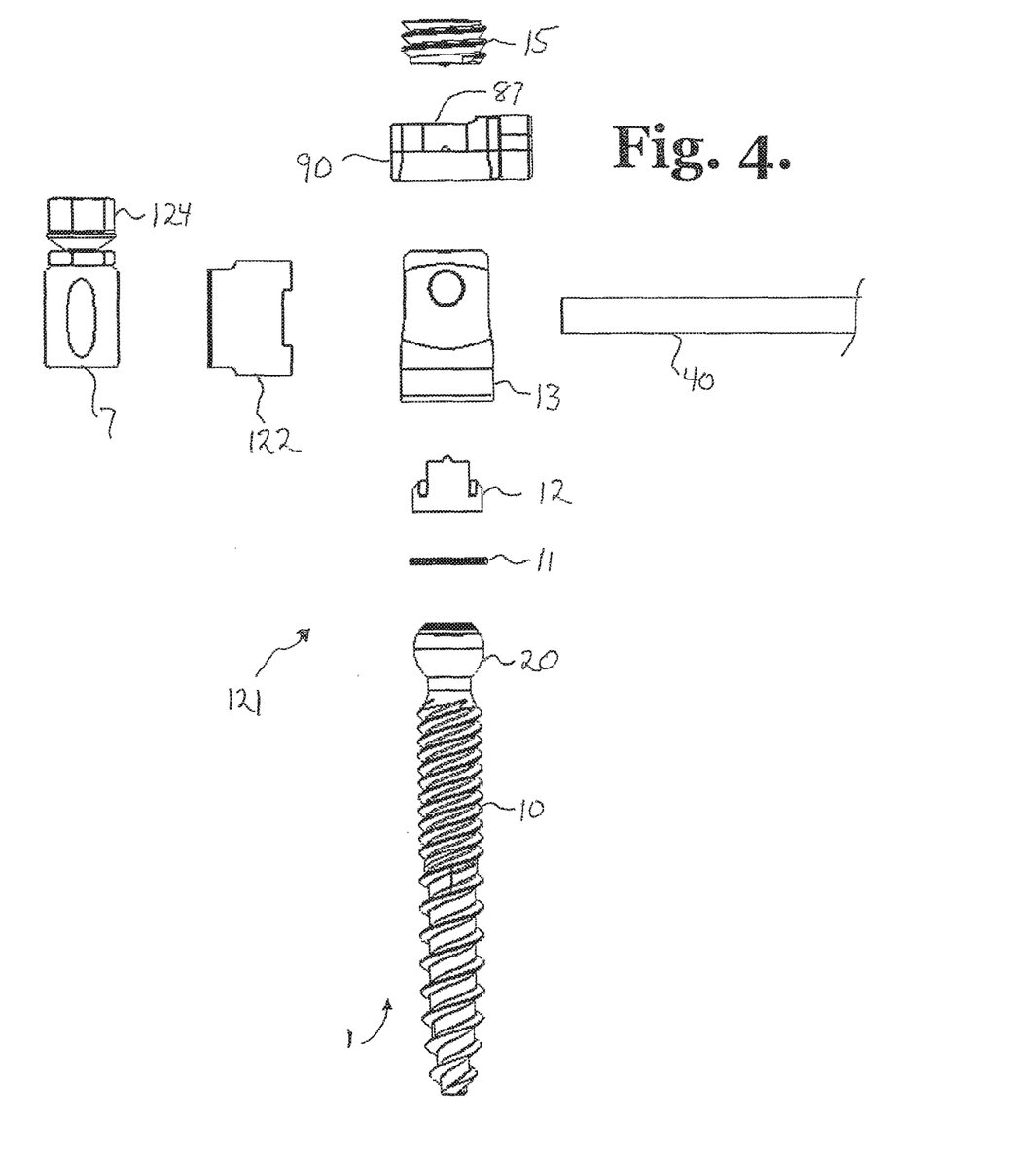
FIG. 4 is an exploded view of a second configuration of a bone screw assembly similar to FIG. 1 with a different sleeve and a bumper/blocker combination.
Figure 5:
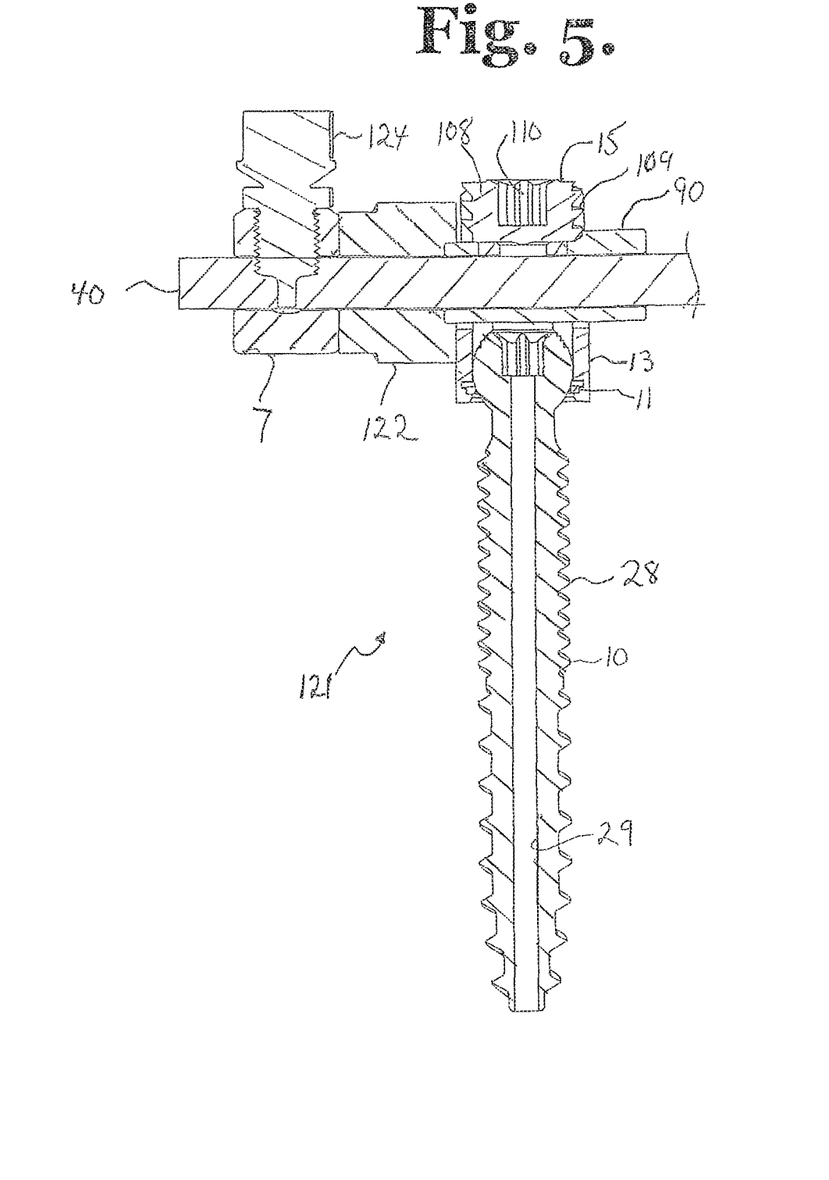
FIG. 5 is a cross sectional view of the assembly shown in FIG. 4 both assembled and vertically cross sectioned.

Shown in FIGS. 4 and 5 is a second configuration 121. The configuration 121 is utilized where the bone anchor 5 is the last in a series of bone anchors 5, here extending to the right. In the configuration 121, a bumper 122 and a blocker 7 are used to secure the elongate member 40, in this embodiment a tensionable cord. The bumper 121 is resilient and compressible and surrounds the elongate member 40 during use while abutting against the bone anchor 5. The blocker 7 receives the elongate member 40 and captures the member 40 therein by compression of a break off set screw 124 configured to penetrate and lock the cord.

In configuration 121 shown in FIG. 4, the second sleeve 90 is utilized and normally a spacer 6 (not shown). Other configurations of the assembly 1 are foreseen.

It is to be understood that while certain forms of the present invention have been illustrated and described herein, it is not to be limited to the specific forms or arrangement of parts described and shown.

What is claimed and desired to be secured by Letters Patent is as follows:

1. A spinal implant sleeve positionable in a channel of a receiver of a bone anchor assembly, the bone anchor assembly including a pressure insert and a bone anchor having a head end opposite an anchor end, with the pressure insert also being positionable in the receiver channel above the head end of the bone anchor, the sleeve comprising:
   a sleeve body constructed of a non-rigid deformable material and having a closed bore extending therethrough for receiving a tensioned cord; and
   a transfer structure constructed of a rigid non-deformable material,
   wherein the transfer structure is incorporated into the sleeve body to receive a force from above the sleeve and transfer the force around the sleeve body of the sleeve and onto the pressure insert positioned within the receiver channel above the head end of the bone anchor.

2. The sleeve of claim 1, further comprising projections extending from the transfer structure to resist torque of the transfer structure relative to the sleeve body.

3. The sleeve of claim 2, wherein the projections extend from the transfer structure into the sleeve body.

4. The sleeve of claim 1, wherein the transfer structure is constructed of a patient implantable metal.

5. The sleeve of claim 4, wherein the transfer structure is constructed of a cobalt chrome alloy.

6. The sleeve of claim 4, wherein the transfer structure is constructed of a metal selected from titanium and titanium alloys.

7. The sleeve of claim 1, wherein the sleeve body is constructed of a thermoplastic polymer.

8. The sleeve of claim 1, wherein the sleeve body is constructed of a polyurethane material.

9. The sleeve of claim 1, wherein the sleeve body is constructed of PEEK.

10. The sleeve of claim 1, wherein the sleeve body is constructed of ultra-high molecular weight polyethylene.

11. A pivotal bone anchor assembly for securing an elongate rod to a bone, the bone anchor assembly comprising:
    a receiver having a channel adapted to receive one of an elongate member and a tensioned cord;
    a pressure insert positioned in the receiver and having upward extending arms and each of the arms having upper surfaces;
    a sleeve positioned in the channel above the pressure insert and in combination with the one of an elongated member and a tensioned cord, the sleeve comprising:
      a sleeve body constructed of a deformable material and having a closed bore extending therethrough for receiving the elongate member or tensioned cord; and
      a transfer structure constructed of a rigid material and having depending legs with lower surfaces that align and mate with the upper surfaces on the pressure insert arms in an overlapping relationship; and
    a closure positioned in the receiver above the sleeve,
    wherein the transfer structure is incorporated into the sleeve body and configured to receive a force from the closure and transfer the force around the sleeve body to the pressure insert without transferring pressure directly through the deformable material of the sleeve body.

12. The bone anchor assembly of claim 11, further comprising projections extending from the transfer structure to resist torque of the transfer structure relative to the sleeve body.

13. The bone anchor assembly of claim 12, wherein the projections extend from the transfer structure into the sleeve body.

14. The bone anchor assembly of claim 11, wherein the transfer structure is constructed of a metal alloy selected from cobalt chrome and titanium alloys.

15. The bone anchor assembly of claim 11, wherein the deformable material is a polymer selected from the group consisting of PEEK, PCU, graphite-filled polyurethane, and ultra high molecular weight polyethylene.

16. The bone anchor assembly of claim 11, further comprising an implantable shank received in the receiver and receiving downward force from the insert.

17. The bone anchor assembly of claim 11, further comprising a retainer positioned within the receiver below the pressure insert and configured to capture and secure a head of an implantable shank within an interior chamber of the receiver.

* * * * *